United States Patent [19]  [11] 4,421,881
Benkendorf et al.  [45] Dec. 20, 1983

[54] NITROCELLULOSE LACQUER COMPOSITION CONTAINING GELATIN AND ACRYLIC COPOLYMERS

[76] Inventors: Sol Benkendorf, 2403 Mountainbrook Dr., Richmond, Va. 23233; Frank A. Calamito, 1 Babbling Brook Rd., Sufferin, N.Y. 10901; Carmine M. Zaccaria, 574 Chestnut St., Westerwood, N.J. 07675

[21] Appl. No.: 369,379

[22] Filed: Apr. 19, 1982

Related U.S. Application Data

[63] Continuation-in-part of Ser. No. 246,836, Mar. 23, 1981, abandoned.

[51] Int. Cl.³ .................. C08L 1/18; C08L 89/06; C08J 3/20
[52] U.S. Cl. .................... 524/24; 524/32; 524/33; 523/105; 424/61; 424/360; 424/362
[58] Field of Search ............ 524/22, 23, 24, 31, 524/32, 33; 424/61, 360, 362; 523/105; 106/128, 195

[56] References Cited

U.S. PATENT DOCUMENTS 2,383,990  9/1945  Quisling .................. 424/61
3,257,280  6/1966  Richter .................. 424/61
3,483,289  12/1969  Michaelson et al. ........ 424/61
3,907,580  9/1975  van Ham .................. 106/158

OTHER PUBLICATIONS

W. C. Doviak "Cosmetics, Science and Technology" 2nd ed. vol. 2, p. 528 (1972) Wiley Interscience Ed., M. S. Balsam et al.

Primary Examiner—John Kight, III
Assistant Examiner—Nathan M. Nutter
Attorney, Agent, or Firm—Cushman, Darby & Cushman

[57] ABSTRACT

An improved nitrocellulose lacquer containing small amounts of water-soluble gelatin of molecular weight range of 15,000 to 250,000 and an acrylic copolymer and a novel process for dispersing and incorporating the gelatin are disclosed.

13 Claims, No Drawings

NITROCELLULOSE LACQUER COMPOSITION CONTAINING GELATIN AND ACRYLIC COPOLYMERS

REFERENCE TO PARENT APPLICATION

This application is a continuation-in-part of U.S. patent application Ser. No. 06/246,836 filed Mar. 23, 1981, now abandoned.

BACKGROUND OF THE INVENTION

1. Field of Invention

This invention relates to novel lacquer compositions which afford desirable improvements in the durability and hardness of the resulting coatings. More particularly, this invention is concerned with novel nitrocellulose-resin based lacquers which contain small amounts of both a high molecular weight mixture of water-soluble gelatins derived from animal bone and hide and an acrylic copolymer and conventional additives. The lacquers are particularly useful for human nail coatings. The novel process for preparing the lacquers involves a novel intermediate which is a solid dispersion of water-soluble gelatin in nitrocellulose.

2. Description of the Prior Art

As is generally known, various base coatings have been prepared and marketed in the past for nail surfacing and various attempts have been made to improve the general performance of coatings which have nitrocellulose as primary film-forming base.

Addition of finely particulated water-insoluble albuminoids such as keratin to nail compositions containing cellulose nitrate and natural or synthetic resins has been disclosed in U.S. Pat. No. 3,483,289.

U.S. Pat. No. 3,907,580 discloses schleroprotein derivatives having such as a collagen hydrolyzate of animal origin with a pH in the range of about 3 to 7.5 in combination with nitrocellulose and an (aryl)sulfonamideformaldehyde resin.

French Patent No. 1.572.598 utilizes an alcohol-soluble protein (collagen) which is specified to be a hydrolyzed gelatin with a molecular weight range of up to 10,000, preferably 500–1000.

The use of methacrylate resins in a cellulose nitrate based fingernail enamel composition is disclosed in U.S. Pat. No. 2,195,971.

While the incorporation of lacquer-insoluble pigments via plasticized nitrocellulose sheet is a known procedure, W. C. Doviak "Cosmetics, Science and Technology", 2nd Ed. Vol. 2, p. 528 (1972), Wiley Interscience Ed. M. S. Balsam et al., this method of dispersing water-soluble gelatin has not heretofore been disclosed.

Prior to the present invention, the joint use of a water-soluble gelatin having molecular weight ranging from 15,000 to 250,000 and an acrylic copolymer to drastically modify and improve the appearance and performance of coatings having the film formers utilized in this invention has not been disclosed. Moreover, in addition to novelty of combination, the method of preparation is also new and novel.

First trials to make a lacquer containing gelatin of the nature envisioned; i.e., water-soluble gelatin of molecular weight 15,000-250,000 derived from a mixture of bone and hide, in combination with the acrylic copolymer met with failure when known methods of incorporating and dispersing collagenous materials of the prior art were applied. To sum up these unsuccessful attempts, the water-soluble gelatin always settled out of the lacquer even after the most vigorous and efficient types of stirring were employed.

As a result of persistent efforts and consideration, methods were found to carry out this invention. These methods utilize high shear grinding of the water-soluble gelatin. This dispersion of gelatin, which is colloidal in nature, can be obtained by conventional means for forming colloid suspensions such as by the use of ball mills or on roller mills. The gelatin is predispersed in the solvents, resins, and plasticizers, which are used in the formulation. One method used to carry out the invention employs coplasticizing in intimate admixture the water-soluble gelatin having a particular molecular weight range and derivation and the nitrocellulose. Preparation of the lacquer of this invention requires predispersion of the gelatin, believed to be of colloidal size, in solid plasticized nitrocellulose mass, a procedure not previously known in the art.

SUMMARY OF THE INVENTION AND OBJECTS

The present invention provides improved novel nitrocellulose-based lacquer compositions especially suitable for application as surface coatings for human nails. The lacquer compositions are free-flowing liquids which may be applied to fingernails and toenails in conventional manner; for example, with a small brush, which provide improved coatings when they harden, being firmly adhering, durable coatings which remain intact for periods of time of at least 3-6 days under a variety of conditions in the environment at home and/or in an office. The cured coatings have a "wet look" of freshly applied lacquer which is retained for extended periods.

The lacquers of this invention are comprised on an overall basis of a primary film former which is nitrocellulose, two or more film formers, one of which is always acrylic copolymer present in proportion of at least about 10% and no more than about 70% by weight of the total secondary film formers specified, water-soluble animal gelatin, suitable plasticizers and liquid carriers therefor, including solvents, couplers and diluents, all of which liquid carriers are for the most part evaporants. Suspension aids may also be added.

By the use of the term "specified water-soluble animal gelatin" throughout the specification is meant Type B gelatin soluble in water and having a molecular weight range of 15,000 to 250,000 and averaging about 50,000 to 70,000 molecular weight and comprised of 50–80 wt. % animal bone-derived gelatin and 20–50 wt. % animal-hide-derived gelatin and unless otherwise stated, this meaning will apply.

The novel process for preparing the nitrocellulose lacquer composition involves intimately predispersing the gelatin in a substantial portion of the nitrocellulose by plasticizing the mixture with a suitable plasticizer and lacquer solvents to form a thick plastic mass and thereafter roller-milling the plastic mass to form a gelatin-nitrocellulose sheet which is cooled and particulated, the particulate being mixed with other lacquer components.

The improvements in properties of adherence to surfaces, durability and the "wet look" are due to the combined effect of the specified water-soluble gelatin and the acrylic copolymer.

As will be readily realized, the process for preparing the lacquer also provides a novel intermediate, the solid dispersion of water-soluble gelatin in nitrocellulose. The process for preparing this intermediate comprises mixing lacquer components comprised of nitrocellulose, a plasticizer, a specified water-soluble gelatin and lacquer solvents to form a plastic mass and thereafter working and spreading the mass under compression and squeezing action, preferably between rollers, to disperse the gelatin and drive off the solvents.

It is therefore an object of the present invention to provide novel lacquer compositions comprised of nitrocellulose primary film-former, two or more resinous secondary film-formers, one of which is always acrylic copolymer, a small amount of specified water-soluble animal gelatin, suitable plasticizers and other conventional lacquer additives and carriers which are especially suitable for human nail coatings.

Another object of this invention is to provide human nail lacquer compositions which cure to coatings of exceptionable hardness and durability and which retain the high gloss appearance of the "wet look" of freshly-applied lacquer.

Another object is to provide a process for preparing uniform and stable nail lacquer compositions containing intimately dispersed specified water-soluble gelatin always in combination in the lacquer with an acrylic copolymer.

Additional objects will become apparent hereinafter and still other objects will be apparent to one skilled in the art.

DETAILED DESCRIPTION OF THE INVENTION

The lacquers of the present invention suitable for human nail colorings and having improved hardness, durability and appearance are comprised of a primary film-former nitrocellulose, two or more resinous secondary film-formers, one of which is always acrylic copolymer, specified water-soluble animal gelatin optionally pigments and coloring agents; plasticizer and a suspending agent, all in liquid carrier vehicle comprised of couplers, diluents and volatile solvents. The acrylic copolymer and water-soluble gelatin serve as modifiers or activators.

In accordance with the present invention, the nail lacquer contains, based on overall weight %, from 10–25%, preferably 15–20% nitrocellulose; from 1–4%, preferably 1.5–2.5 wt. % acrylic copolymer resin; from 5 to 10%, preferably 7 to 8% secondary film-forming resin other than acrylic copolymer or a synthetic modified resin; from 0.25–1.0%, preferably 0.4 to 0.8 wt. % specified water-soluble animal gelatin; 4–8%, preferably 5–7% plasticizer and the balance liquid carrier vehicle including couplers, solvents and diluents.

The nitrocellulose used is lacquer grade nitrocellulose, preferably of the type "RS" or "SS" and in particular nitrocellulose type RS ¼ seconds, nitrocellulose type RS ½ seconds and nitrocellulose RS type ¾ seconds. The "RS" type nitrocelluloses are preferred, type RS ½ second being preferred over all others. The commercially available cellulose nitrates (RS, AS and SS) with viscosity and nitrogen content ranges are described by G. N. Bruxelles and V. C. Grassie in N. M. Bikales, Ed. *Encyclopedia of Polymer Science and Technology*, Vol. 3, Interscience Publishers, a division of John Wiley and Sons, Inc., N. York (1965) pp 307–325. Viscosity is measured in seconds of time it takes a falling ball of specified metal and size to fall a definite measured distance through a specified concentration of nitrocellulose while the nitrocellulose solution is confined in a glass tube of uniform and definitely described diameter and while the temperature of the liquid is held within strictly described limits. The test is described at pages 39 and 40 of *Nitrocellulose Handbook*, Hercules Corp., Wilmington, Del. (1979). If ¼, ½, ¾ sec. grades of nitrocellulose are dissolved at 12.2% by weight in a standard test solvent with composition as follows,

|  | Percent by weight |
|---|---|
| Denatured ethyl alcohol | 25 (190 proof) |
| Toluene | 55 (Industrial pure) |
| Ethyl acetate | 20 (85–88%) |
| Total | 100 | a 3/32 inch steel ball will fall through 2 inches of the solution in approximately ¼, ½ and ¾ seconds, respectively.

In addition to acrylic copolymer which is always present, the secondary film-forming resins suitable for the practice of this invention may be selected from one or more of the following synthetic resinous material: arylsulfonamide formaldehyde, vinyl, vinylidene, alkyd, epoxy, melamine, phenolic, polyester, polyurethane, urea formaldehyde, polyethylene, polystyrene and polypropylene and the natural dammar resin. The synthetic resins are preferred and of these the preferred secondary film-forming resin used in conjunction with acrylic copolymer is an arylsulfonamide formaldehyde resin. Suitably, the arylsulfonamide formaldehyde resin is a naphthyl, phenyl or substituted phenyl sulfonamide. Preferably, the arylsulfonamide resin used in lacquers of this invention is toluenesulfonamide formaldehyde resin.

Plasticizing agents usable in the lacquers are such as tricresyl phosphate, benzyl benzoate, tributyl phosphate, butyl acetyl ricinoleate glyceryl acetyl rincinoleate, dibutyl phthalate, dibutyl glycolate, dioctyl phthalate, butyl stearate, tributoxy ethyl phosphate, triphenyl phosphate, triethyl citrate, tributyl citrate, tributylacetyl citrate, 2-hexyl triethyl acetyl citrate, dibutyl tartrate, dimethoxy ethyl phthalate, di-isobutyl phthalate, diamyl phthalate, camphor and various mixtures thereof. Of these, dibutylphthalate plasticizer is preferred, preferably along with a small amount of camphor.

The specified water-soluble gelatins suitable for practicing the invention are prepared by the procedures described in Kirk Othmer Encyclopedia of Chemical Technology 11, 711–19 (1980). As stated above, the gelatin is a mixture of 50–80% bone gelatin and 20–50% hide gelatin. The preferred ratio range is 65–70% bone gelatin to 25–35% hide gelatin. When the ratio of bone to hide gelatin is above about 80%, the product becomes gritty on standing and wear resistance is too low. These effects are illustrated in Examples 6–9. See also Table 2.

When the proportion of acrylic copolymer of the total secondary film-former is below about 10%, there is no significant improvement in durability of the dried coatings. When the proportion of acrylic copolymer of the total secondary film-former is above about 70%, the lacquer is too thick and hard to control. Also, wear resistance decreases in proportion to added acrylate in excess of about 4.0 wt. % based on total lacquer weight. The effect of adding too much acrylate is illustrated in Examples 12a and 12b. See also Table 3.

By acrylic copolymer is meant a polymerized combination selected from among acrylic, methacrylic, 2-hydroxyl ethyl methacrylic acids, their esters, amides and alkali metal and ammonium salts and the like. Examples of suitable combinations are (1) acrylamide-sodium acrylate copolymer
(2) acrylate-acrylamide copolymer
(3) acrylate-ammonium methacrylate copolymer
(4) acrylates-copolymer
(5) acrylic-acrylate copolymer which is an acrylic acid and methacrylic acid or an ester The one preferred is acrylates-copolymer, which is a polymer of two or more monomers consisting of acrylic acid and methacrylic acid and simple esters thereof.

Among the solvents usable in the compositions of the lacquers, a few in particular are cited: ethyl acetate, butyl acetate, amyl acetate, methylacetate, methylisobutylketone, methylethyl, ketone, methyl glycol acetate and mixtures of such solvents. Preferably, a mixture of butyl and ethyl acetates is used in mixture.

Among the so-called couplers, the lower molecular weight alkanols may be used such as ethanol, propanol, isopropyl alcohol, n-butyl alcohol and mixtures thereof. Preferably, a mixture of isopropyl alcohol and n-butyl alcohol are used.

As diluents, aromatic or aliphatic hydrocarbons such as toluene or heptane may be used or a mixture thereof. Preferably, the diluent used is toluene. Inorganic pigments such as titanium dioxide, colored polymeric material and dyes may be used for color effects.

Process Description

In general, the process for preparing the lacquers of this invention comprises working a mixture comprised of water-soluble gelatin, nitrocellulose plasticizer and lacquer solvents under compression to intimately disperse the gelatin, driving off the solvents to form a solid predispersion comprising gelatin dispersed in nitrocellulose and plasticizer and thereafter combining the solid predispersion in particulate form with lacquer components, among which are two or more secondary film formers, one of which is always acrylic copolymer.

More specifically, the process for the preparation of a nitrocellulose lacquer containing water-soluble gelatin and acrylic copolymer comprises the steps of (1) mixing lacquer components comprised of specified water-soluble gelatin, a portion of the total plasticizer and sufficient lacquer solvents to give a high viscosity liquid, (2) working the high viscosity liquid obtained in step 1 under compression and squeezing motion, preferably on a roll-mill, to disperse the gelatin and form a solid predispersion comprised of nitrocellulose, gelatin and plasticizer, preferably as a sheet or ribbon, (3) particulating the solid from step 2, preferably by grinding in at least a portion of lacquer liquids and (4) mixing and/or further particulating solids from step 3 with the balance of the lacquer ingredients which include acrylic copolymer and another secondary film-former.

A general description of the individual steps of the process follows:

In step (1) the gelatin is mixed with about 4 to 30 times, preferably about 7-8 times, its weight of nitrocellulose and about 1 to 6 times, preferably about 1 to 2 times, its weight of plasticizer, preferably dibutylphthalate together with sufficient lacquer solvents and liquids to form a high viscosity liquid. The lacquer solvents preferably are used in the same or about the same ratio as in the basic overall finished formulation used to make a particular lacquer. Obviously, because the solvents are evaporated for the most part in the next step, many equivalent variations will be apparent, including the use of some which are not used in quantity in the final product.

In step (2) high viscosity liquid is worked by spreading the mass from step (1) under compression and squeezing action, preferably between water-cooled rollers of a roller mill in repetition until the gelatin has become intimately dispersed. Illustratively, about 3 to 4 passes through a 2-roll water-cooled roller mill will be sufficient.

In step (3) the gelatin-nitrocellulose dispersion is particulated in at least a portion of the lacquer liquids. The proportion of lacquer liquid to the total lacquer liquids may vary over a wide range up to and including the the total liquids. The nitrocellulose-gelatin dispersion is comprised of three major components ranging in proportions, in parts by weight, of 3-17 gelatin, preferably about 10 gelatin; about 69-81 nitrocellulose, preferably about 75 nitrocellulose; and about 14-16 plasticizer, preferably about 15 plasticizer. These ranges are exclusive of small amounts of solvents which remain trapped in the solid sheet.

In step (4) a clear lacquer base comprised of 75% of the solvents and diluents portion of the formula are placed in a mixing tank. Under agitation with a high-shear mixer, nitrocellulose is first added and dissolved followed by addition of gelatin dispersion prepared in step (3), the secondary film-forming resins including acrylic copolymer and remaining plasticizer and suspending agent. Sufficient time of mixing is allowed to insure homogenuity. Color dispersions are optionally added, viscosity is adjusted to requirement and the lacquer is filtered.

Obviously, many variations in order of addition will become apparent to those skilled in the art.

The novel lacquer compositions of the present invention and the method of preparation are exemplified more fully by the folowing illustrative and comparative examples. The scope of the invention is, however, not limited to the illustrative examples.

EXAMPLE 1

(Gelatin and Acrylic Copolymer)

A lacquer composition having the following overall composition was prepared by the method following.

| Ingredient | Weight % of Ingredient in Finished Lacquer |
| --- | --- |
| Nitrocellulose, RS ½ Sec. | 17.50 |
| Toluenesulfonamide formaldehyde resin | 7.50 |
| Gelatin (a) | 0.60 |
| Dibutyl phthalate | 5.00 |
| Acrylates-copolymer | 2.00 |
| Camphor | 0.55 |
| Butyl acetate | 17.50 |
| Ethyl acetate | 7.50 |
| Isopropyl alcohol | 5.00 |
| n-Butyl alcohol | 0.55 |
| UV Absorber | 0.05 |
| Toluene | 36.25 |

| Ingredient | Weight % of Ingredient in Finished Lacquer |
|---|---|
| | 100.00 |

(a) Type B gelatin: Manufacturer's specification for derivation of gelatin is 70% bone; 30% hide. The molecular weight ranges from 15,000–250,000. The average molecular weight in several determinations by high pressure liquid chromatography was found to range from 62,000 to 73,000.

(Predispersion of Gelatin in Plasticized Nitrocellulose)

A solid dispersion of gelatin in nitrocellulose was prepared as follows: A charge of all the gelatin, 9 times its weight of nitrocellulose, 3 times its weight of dibutylphthalate, together with sufficient lacquer solvents preferably in the overall proportions contained in the finished lacquer to wet the mass was mixed in a High Shear Cowles mixer to give a high viscosity liquid. The mass was charged onto the rolls of a high-speed, water-cooled roller mill and the high viscosity liquid was recycled through the roll mill until the maximum dispersion was obtained.

(Preparation of Lacquer Base)

To 70% of the solvents in the ratio required in the above formulation held in a tank under high-shear agitation (i.e., Hochmeyer ® Dispenser) was added the remainder of nitrocellulose not used in making the gelatin nitrocellulose chip. When the nitrocellulose had dissolved, the toluene sulfonamide formaldehyde resin, the remainder of the dibutyl phthalate, camphor and UV absorber were added in sequence. Agitation was continued until ingredients were substantially dissolved. The solution was filtered to remove traces of impurity and the acrylates-copolymer was added under agitation.

(Preparation of Finished Lacquer)

The gelatin-nitrocellulose dispersion prepared above was dispersed in the remaining 30% of the solvents under high shear agitation and added to the foregoing lacquer base under agitation. The lacquer was filtered.

Comparative Examples 2–4

Lacquer compositions for comparative purposes were prepared following:

| Ingredient | Example 2 Gelatin- (No Acrylate) | Example 3 Acrylate- (No Gelatin) | Example 4 (No Gelatin- No Acrylate) |
|---|---|---|---|
| Nitrocellulose, RS ½ Sec. | 17.50 | 17.50 | 17.50 |
| Toluenesulfonamide formaldehyde resin | 7.50 | 7.50 | 7.50 |
| Gelatin (a) | 0.60 | — | — |
| Dibutylphthalate | 5.00 | 5.00 | 5.00 |
| Acrylates-copolymer | — | 2.00 | — |
| Camphor | 0.55 | 0.55 | 0.55 |
| Butyl acetate | 17.50 | 17.50 | 17.50 |
| Ethyl acetate | 7.50 | 7.50 | 7.50 |
| Isopropyl alcohol | 5.00 | 5.00 | 5.00 |
| n-Butyl alcohol | 0.55 | 0.55 | 0.55 |
| UV Absorber | 0.05 | 0.05 | 0.05 |
| Toluene | 38.25 | 36.85 | 38.85 |
| Total | 100.00 | 100.00 | 100.00 |

(a) Same as Example 1.

The lacquer of Example 2 was prepared by the same procedure as Example 1, except no acrylic copolymer was added. The composition of Example 3 required no gelatin dispersion and was prepared as described in Example 1 under "Preparation of Lacquer Base," using all the solvent, plasticizer and nitrocellulose in that step and the lacquer base was the finished lacquer. The composition of Example 4 having neither gelatin nor acrylic monomer was prepared as in Example 3, except no acrylic was added.

Example 5

A lacquer composition having the following overall composition was prepared by the method following:

| Ingredient | Weight % of Ingredient In Finished Lacquer |
|---|---|
| Nitrocellulose, RS ½ Sec. | 17.50 |
| Toluenesulfonamide formaldehyde resin | 7.00 |
| Gelatin (a) | 0.66 |
| Dibutyl phthalate | 5.25 |
| Acrylates-copolymer | 2.00 |
| Camphor | 1.00 |
| Butyl acetate | 20.00 |
| Ethyl acetate | 7.00 |
| Amyl acetate | 5.00 |
| Isopropyl alcohol | 5.00 |
| n-Butyl alcohol | 1.00 |
| UV Absorber | 0.05 |
| Toluene | 25.50 |
| Stearalkonium hectorite (Clay suspension agent) | 1.04 |
| Pigment dispersion | 2.00 |
| Total | 100.00 |

(a) Same as Example 1.

Predispersed gelatin-nitrocellulose chip was prepared as in Example 1. Lacquer base was also prepared in Example 1, except a small portion of the nitrocellulose and solvent was withheld and used to mix with and form a suspension with the clay suspension agent. The acrylic copolymer was then added to this suspension which was in turn added to the lacquer base. The lacquer was then finished as in Example 1 by adding the gelatin-nitrocellulose dispersion into the lacquer base and finally adding the pigment dispersion and filtering. Example 1 and comparative Examples 2–4 were evaluated by and compared in mechanical testing procedure as follows:

Mechanical Test-Procedure

General Description: Preformed acrylic "Pinback" paintable nails are twice coated with nail lacquer using a small brush, dried for 24 hours and tumbled with sand in tubes mounted on a rotating bar for a given period of time. The coatings are then observed, scored and evaluated to obtain a "Wear Index." The lower the "Wear Index", the better the coating.

Coating Procedure: Blank #3 "Pinback" acrylic nails used in the trade to display various nail polishes are fixed in place in rows via the raised knob on the back of the nails so that the rounded surface is face up on a ⅜" thick flat acrylic sheet. The raised knobs fit into holes drilled in an acrylic sheet. The nails are then painted using a nail polish brush, dipping from a small nail polish bottle which has been shaken first, always dipping the brush once per nail and uniformly coating the surface and edge. The nails are painted a second time allowing a suitable amount of time between coats for drying and a minimum of 24 hr. after the last coat. The coated nails are removed from the acrylic sheet for testing.

Abrasion Test Apparatus and Procedure

Capped 50 ml tubes (1" I.D.) are loaded with 5 g sea sand (Fisher Scientific, washed and ignited) and 5 coated nails. The tubes are mounted vertically with clamps to a mechanically rotatable bar. The bar with tubes attached containing the sand and nails is rotated for 18 hours at 20 rpm, each revolution moving sand and nails from one end of the tube to the other. A total of 15 painted nails were used in each evaluation.

Test Evaluation Procedure

Nails are removed from the tubes and separated from the sand. Each nail is visually observed individually and given a grade from 0 to 5 as follows:

| | |
|---|---|
| 0 | unabraided (control) |
| 1 | slight body and edge wear |
| 2 | slight to moderate body and edge wear |
| 3 | moderate body wear and loss of shine with slight chipping |
| 4 | moderate to severe body wear, loss of shine, chipping without bare spots* |
| 5 | severe body wear with bare spots* and extensive edge wear |

*bare spot - an area where the coating has been worn away, revealing the underlying surface of the original unpainted nail.

The "Wear Index" is determined by multiplying the number of nails at each grade level by the grade number, adding the total and dividing by the total number of nails treated. Results of tests on 15 nails for each of Examples 1-4 are in Table 1.

TABLE 1

| | | Abrasion Resistance Tests | | | | | | |
|---|---|---|---|---|---|---|---|---|
| Example No. | Significant Characteristic of Lacquer Composition | No. out of 15 at Each Grade Level | | | | | | Wear Index |
| | | 0 | 1 | 2 | 3 | 4 | 5 | |
| 1 | Gelatin & acrylic | 0 | 6 | 5 | 4 | 0 | 0 | 1.86 |
| 2 | Gelatin - no acrylic | 0 | 3 | 5 | 5 | 2 | 0 | 2.40 |
| 3 | Acrylic - no gelatin | 0 | 0 | 3 | 8 | 4 | 0 | 3.07 |
| 4 | No gelatin - no acrylic | 0 | 0 | 5 | 10 | 0 | 0 | 2.67 |

As can be observed, the "Wear Index" obtained with the lacquer having the combination of gelatin and acrylic copolymer was superior to lacquers having gelatin alone, acrylic copolymer alone or lacquer having neither gelatin nor acrylic copolymer.

Comparative Example 6

(Attempt to Prepare Lacquer from all Bone-Gelatin, Type B)

The procedure of Example 1 was attempted, except the same amount of a commercial Type B gelatin derived entirely from bone in the initial step was substituted for the bone-hide gelatin of Example 1. However, the gelatin did not disperse in the nitrocellulose using the roll-mill.

Comparative Example 7

(Lacquer Prepared from all Bone-Gelatin, Type B)

The procedure of Example 1 was followed, except the same amount of another commercial Type B gelatin derived from bone (distinct from the bone gelatin used in Example 6) was substituted for the bone-hide gelatin in the formulation of Example 1. Dispersion of the gelatin in the nitrocellulose appeared to be successful; however, the final product on standing became gritty and was unacceptable for use as a fingernail polish.

Comparative Example 8

(Lacquer Prepared from all Hide Gelatin, Type B)

The procedure of Example 1 was followed, except the same amount of a commercial Type B gelatin derived entirely from animal hide was substituted for the bone-like gelatin in the formulation of Example 1. The finished product was comparable in appearance to that prepared in Example 1 and did not become gritty on standing. However, in a blind test as fingernail polish on 10 women, the wear resistance was very poor, the time before the enamel began to chip off being only a fraction (less than one day; i.e., less than about 25%) of that observed with the product of Example 1 (3-4 days) in the same blind test.

Comparative Example 9

(Lacquer Prepared from Pork Skin, Type A)

The procedure of Example 1 was followed, except the same amount of a commercial Type A gelatin derived entirely from pork skin was substituted for the bone-hide gelatin in the formulation of Example 1. The finished product was comparable in appearance to that prepared in Example 1 and did not become gritty on standing. However, in a blind test as finger nail polish on 10 women, the wear resistance was very poor, the time before the enamel begain to chip off being only a fraction (less than one day; i.e., less than about 20%) of that observed with the product of Example 1 (3-4 days) in the same blind test.

Critical variants and results obtained with enamel prepared in Examples 6-9 are compared to those with Example 1 in Table 2.

TABLE 2

(Summary of Variations Due to Gelatin Type and Source)

| | | Result | |
|---|---|---|---|
| Example No. | Type of Gelatin and Derivation | Appearance of Product | Fingernail Wear Resistance Time Before Chipping, **Days |
| 1 | B - 70% bone - 30% hide | smooth | 3-4 |
| 6 | B - 100% bone | Gelatin did not disperse in nitrocellulose | — |
| 7 | B - 100% bone | gritty* | *** |
| 8 | B - 100% hide | smooth | less than 1 |
| 9 | A - pork skin | smooth | less than 1 |

*Nail enamel became gritty due to precipitation of hard solid on standing after filtration.
**Avg. 10 women each product tested.
***Too gritty for reasonable use.

Examples 10a and 10b

Lacquers were prepared by the procedure of Example 1 but substituting 0.3 parts by weight and 0.9 parts by weight, respectively, of the same gelatin as used in Example 1 rather than the 0.6%, keeping all other ingredients in the same ratio. In a blind test, as fingernail polish on 10 women, the time before the enamel began to chip off was about the same compared with the product of Example 1 in the same blind test; i.e., 3-4 days.

Examples 11a and 11b

Lacquers were prepared by the procedure of Example 1, 10a and 10b using the same amounts of gelatin as in Examples 10a and 10b but substituting 6.0 % by weight of the same acrylate copolymer for the 2% amount. In a blind test as fingernail polish on 10 women, the time before the enamel began to chip off was about the same compared with the product of Example 1 in the same blind test; i.e., 3-4 days.

Examples 12a and 12b

Lacquers were prepared by the procedure of Example 1 using the same amounts of the same gelatin as in Example 10a and 10b but substitutiing 6.0% by wt of the same acrylate copolymer for the 2% amount. In a blind test as fingernail polish on 10 women, the time before the enamel began to chip off was about one day compared to the product of Examples 1 of 3-4 days in the same blind test.

Critical variants and results in Examples 10a, 10b, 11a, 11b, 12a and 12b compared to Example 1 are summarized in Table 3.

TABLE 3
(Effect of Acrylate Variation)

| Example No. | Weight % Gelatin in Nail Lacquer | Weight % Acrylate in Nail Lacquer | Fingernail Wear Resistance Time Before Chipping *Days |
|---|---|---|---|
| 1 | 0.6 | 2.0 | 3-4 |
| 10a | 0.3 | 2.0 | 3-4 |
| 10b | 0.9 | 2.0 | 3-4 |
| 11a | 0.3 | 4.0 | 3-4 |
| 11b | 0.9 | 4.0 | 3-4 |
| 12a | 0.3 | 6.0 | Less than 1 |
| 12b | 0.9 | 6.0 | Less than 1 |

*Avg. 10 women each product.

Various modifications and equivalents will be apparent to one skilled in the art and may be made in the lacquer composition and methods of preparation of the present invention without departing from the spirit or scope thereof and it is therefore understood that the invention is to be limited only by the scope of the appended claims.

What is claimed is:

1. A lacquer composition, comprising:
A. a nitrocellulose primary film former,
B. at least two resinous secondary film-formers, one of said at least two secondary film formers being acrylic copolymer present in an amount between about 10% and about 70% by weight based on the total of secondary film formers, and in an amount less than about 4% based on the weight of said lacquer composition,
C. a Type B water-soluble animal gelatin prepared by alkaline hydrolysis of animal bone and hide, wherein said gelatin has a molecular weight range of 15,000 to 250,000 and an average molecular weight of 50,000 to 70,000, and wherein said gelatin comprises:
  (i) 50-80 weight % animal bone-derived gelatin,
  (ii) 20-50 weight % animal hide-derived gelatin,
D. plasticizer, and
E. liquid carrier.

2. The lacquer composition of claim 1 wherein the gelatin is 65-75% bone gelatin and 25-35% hide gelatin.

3. The lacquer composition of claim 1 wherein said gelatin content is 0.25 to 1.0 wt. % and the acrylic copolymer content is 1 to 4 wt. %.

4. The lacquer composition of claim 1 wherein the gelatin content is 0.4 to 0.8 wt. % and the acrylic copolymer content is 1.5 to 2.5 wt. %.

5. The lacquer composition of claim 1 wherein the resinous secondary film former used in addition to acrylic copolymer is toluene sulfonamide formaldehyde resin.

6. A process for preparing a nitrocellulose lacquer containing gelatin and acrylic resin which comprises working a mixture comprised of gelatin, nitrocellulose, plasticizer and lacquer solvents under compression to intimately disperse the Type B water-soluble animal gelatin, driving off the solvents to form a predispersion comprising gelatin dispersed in nitrocellulose and plasticizer and thereafter combining said predispersion in particulate form with lacquer components among which are two or more resinous secondary film formers, one of which is always acrylic copolymer, said gelatin comprised of 50-80weight % animal-bone-derived gelatin and 20-50 weight % animal-hide-derived gelatin.

7. A process for the preparation of a nitrocellulose lacquer containing water-soluble gelatin which comprises the steps of
(1) mixing lacquer components comprised of Type B water-soluble animal gelatin of molecular weight range 15,000 to 250,000 and averaging about 50,000 to 70,000 molecular weight, a portion of the total plasticizer lacquer solvents to give a high viscosity liquid, said gelatin comprised of 50-80 weight % animal-bone-derived gelatin and 20-50 weight % animal-hide-derived gelatin,
(2) working the high viscosity liquid obtained in step 1 under compression and squeezing motion to disperse the gelatin and form a predispersion comprised of nitrocellulose, gelatin and plasticizer,
(3) particulating the mass from step 2, and
(4) mixing and/or further particulating the mass from step 3 with the balance of the lacquer ingredients among which are two or more resinous secondary film formers, one of which is always acrylic copolymer.

8. The process of claim 7 wherein in step 2 the high viscosity liquid is worked on a roll mill.

9. The process of claim 7 wherein in step 3 the mass is particulated by grinding in at least a portion of the lacquer liquids.

10. The process of claim 7 wherein the amount of said gelatin added based on the weight of finished lacquer is 0.25 to 1.0 wt. % and the amount of acrylic copolymer is 1 to 4 wt. %.

11. The process of claim 7 wherein the amount of said gelatin added based on the weight of the finished lacquer is 0.4 to 0.8 wt. % and the amount of acrylic copolymer is 1.5 to 2.5 wt. %.

12. A colloidal dispersion of animal gelatin in plasticized nitrocellulose, said animal gelatin present in an amount of 3 to 17 wt. % and having molecular weight range of 15,000 to 250,000 and averaging about 50,000 to 70,000 molecular weight comprised of 50-80 weight % animal bone-derived gelatin and 20-50 weight % animal hide-derived gelatin.

13. A process for preparing a dispersion of water-soluble gelatin in nitrocellulose which comprises mixing lacquer components comprised of nitrocellulose, a plasticizer, a water-soluble gelatin having molecular weight range of 15,000-250,000 and lacquer solvents to form a plastic mass and thereafter working and spreading the mass under compression and squeezing action to disperse the gelatin and drive off the solvents, said gelatin comprised of 50-80 weight % animal bone-derived gelatin and 20-50 weight % animal hide-derived gelatin.

* * * * *